United States Patent [19]

Jessop

[11] Patent Number: 4,840,074
[45] Date of Patent: Jun. 20, 1989

[54] MULTI-STREAM FLUID SAMPLING VALVE

[75] Inventor: Paul A. Jessop, Northwich, England

[73] Assignee: VG Instruments Group Limited, Crawley, England

[21] Appl. No.: 175,847

[22] Filed: Mar. 31, 1988

[30] Foreign Application Priority Data

Apr. 2, 1987 [GB] United Kingdom ............... 8707874

[51] Int. Cl.⁴ ............................................. G01N 1/00
[52] U.S. Cl. ............................ 73/864.81; 73/863.33; 73/863.56
[58] Field of Search ........... 73/863.56, 863.45, 863.55, 73/863.44, 863.73, 864.81, 863.51, 863.52, 863.53, 863.81, 863.82, 863.58, 863.33

[56] References Cited

U.S. PATENT DOCUMENTS

| | | | |
|---|---|---|---|
| 2,721,578 | 10/1955 | Pouppirt | 137/637 X |
| 3,209,343 | 9/1965 | Dunham et al. | 340/618 X |
| 3,425,446 | 2/1969 | McNown | 251/331 X |
| 3,757,583 | 9/1973 | Ludewig | 73/863.33 |
| 3,827,302 | 8/1974 | Sato | 73/863.33 |
| 4,113,434 | 9/1978 | Tanaka et al. | 73/863.55 |
| 4,156,437 | 5/1979 | Chivens et al. | 137/554 |
| 4,601,211 | 7/1986 | Whistler | 73/863.33 |

FOREIGN PATENT DOCUMENTS 1259605 1/1968 Fed. Rep. of Germany .
1334431 10/1973 United Kingdom .

Primary Examiner—Stewart J. Levy
Assistant Examiner—Michele Simons
Attorney, Agent, or Firm—Chilton, Alix & Van Kirk

[57] ABSTRACT

The invention provides a sample valve adapted to produce a sample of any one of a plurality of fluid streams for an analytical instrument (especially a mass spectrometer). It comprises a stationary plate member in which are formed a plurality of inlet ports. A sampling head is mounted from a drive shaft which is rotated to select one of the inlet ports. A sample of the fluid flowing through the selected inlet is taken by a narrow-bore pipe and is transferred via a rotary shaft sealing means to a stationary output member. Excess gas from the selected inlet port passes inside a sleeve member in the sampling head and into a purging chamber adjacent to the exterior of the sealing means, thereby minimizing contamination of the sample through a leak in the sealing means.

20 Claims, 2 Drawing Sheets

MULTI-STREAM FLUID SAMPLING VALVE

BACKGROUND OF THE INVENTION

1. Field of the Invention

This invention relates to apparatus for sampling fluids, and in particular to a sample valve adapted to select a portion of a flow from any one of a number of streams in order to provide a continuously flowing sample for an analytical instrument such as a mass spectrometer.

2. Description of the Prior Art

Several types of valves adapted for this purpose are known in the art. For example, systems involving a plurality of valves are described in U.S. Pat. Nos. 3,757,583, 2,721,578, and 3,827,302, and U.S. Pat. No. 3,209,343 describes a sampling system incorporating a rotary selection valve which is not described in detail.

A diaphragm type valve is shown in U.S. Pat. No. 3,425,446. Detailed descriptions of rotary selection valves are given in UK Pat. No. 1,334,431, German Pat. No. 1,259,605, and U.S. Pat. No. 4,156,437. These valves comprise a plurality of feedpipes connected to ports in a flat plate, and a rotor maintained in sealing contact with the plate. A stream is selected through channels cut in the rotor. U.S. Pat. No. 4,601,211 describes a valve in which selection is achieved by alignment of a flexible tube with a port through which gas to be sampled is flowing.

Especially in the case of an analytical instrument which requires only a small fraction of the flow available at each inlet, it is very important that the dead volume and the leak rate of the valve are kept to a minimum. Systems which incorporate a plurality of separate valves usually have dead volumes which are too high to allow their use with very low sample flow rates, and special precautions have to be taken in the design of rotary sampling valves to minimize contamination of the sample through leaks. In some prior valves, the region of the face-to-face seal between the rotor and the flat plate is purged by a separate supply of a purging gas introduced into a port in the valve body. However, the need for a separate supply of a suitable purging gas limits the use of valves of this type.

In the case of the valve described in U.S. Pat. No. 4,601,211 the face-to-face seal between the rotor and the flat plate is eliminated, so that there is no need for a supply of purging gas. A problem encountered with this valve is that the lifetime of the flexible tube, which undergoes continuous flexing in the same place as the valve operates, is limited.

SUMMARY OF THE INVENTION

It is the object of the present invention to provide a reliable multi-stream flow sampling valve which has a low dead volume and in which contamination of the selected sample output by any other sample fluid or the atmosphere in which the valve operates is reduced to a very low level.

In accordance with this object there is provided a valve for providing a sample from any one of a plurality of streams of fluid, comprising movable selecting means for selecting one of said plurality of streams while allowing the unselected ones of said streams to discharge, sample dividing means for dividing the selected one of said streams into a sample flow portion and a purging flow portion, a transfer member movable with said selecting means and adapted to convey said sample flow portion from said selecting means to a stationary output member, sealing means for connecting said transfer member to said stationary output member and adapted to confine substantially all of said sample flow portion to its interior, a movable seal housing in which said sealing means is disposed, a purging chamber formed in said seal housing adjacent to at least a part of the exterior of said sealing means, and means for passing said purging flow portion through said purging chamber.

Preferably the valve is adapted to work with gaseous streams and to provide a sample of gas suitable for an analytical instrument, especially a mass spectrometer. In a preferred embodiment, the selecting means comprises a movable sampling head capable of being positioned in alignment with any selected one of a plurality of ports provided in a stationary plate member, to which ports the streams of fluid to be sampled are supplied. The sampling head may conveniently comprise a sleeve member of internal diameter greater than that of the ports, which is slidably mounted in the head and arranged so that its end is maintained in substantially sealing contact with the plate. In this way the selected sample flows through the sleeve member into the sampling head. Means, preferably a spring fitted inside the sampling head, are provided to maintain the sleeve member in contact with the stationary plate member.

The sample dividing means preferably comprises a first tube member, preferably a narrow-bore tube fitted concentrically in the sleeve member with its end just short of the end of the sleeve member when the sleeve member is engaged with the plate. The selected stream is thereby divided into a sample flow portion which enters the first tube member and a purging flow portion which flows around the exterior of the first tube member and inside the sleeve member. The first tube member is connected to the transfer member which in turn is connected to the output member via the sealing means. The bore of the first tube member is selected to ensure the desired flow rate of sample from the output member.

According to the invention, at least a part of the exterior of the sealing means is exposed to a purging chamber which is filled with the purging flow portion of the selected stream. In this way, contamination of sample flowing in the output member either by gas from any of the unselected sample streams or by the atmosphere due to a leak in the sealing means is substantially prevented. Consequently, there is no need for a very high performance seal at this point, even if the pressure inside the seal is reduced below that in the purging chamber by virtue of the effect of the analytical instrument connected to the output member, because the composition of the sample and purging flow portions is substantially identical. In prior valves where purging with the sample gas is not provided, even a small leak into the sample stream can result in serious contamination of the sample, because the sample output flow is usually considerably less than 1 ml/minute, especially when a mass spectrometer is used as the analytical instrument.

Further, the seal between the stationary plate member and the sleeve member does not need to be of a very high quality, because the flow rate at the inlet ports is usually many times greater than that of the sampled portion. It is therefore of little consequence if a considerable portion of the stream escapes through a leak between the sleeve member and the stationary plate member, and the risk of contamination of the sample flow portion is minimized because it is sampled from the centre of the inlet port by the first tube member. A similar principle is exploited in the valve described in U.S. Pat. No. 4,601,211 where no attempt is made to seal the flexible sampling tube to the inlet port.

In a further preferred embodiment the movable seal housing is connected to a hollow rotatable drive shaft, and the sampling head is mounted on a rigid second tube member attached to the drive shaft. The drive shaft is supported in suitable bearings, and the rigid tube extends radially of the drive shaft. At least a part of the stationary output member is disposed concentrically within the drive shaft, and another bearing is provided for the drive shaft on the output member. The rigid second tube member may then be used to convey the purging flow portion of fluid from the dividing means to the purging chamber.

Preferably the seal housing is formed in the end of the drive shaft itself. The output member, circular in cross section, extends into the purging chamber and is aligned with the transfer member, which preferably comprises a tube of the same external diameter, connected to the first tube member of the dividing means. The sealing means typically comprises a lipped rotary rubber or PTFE seal which extends over the ends of the output member and the transfer member and which is fitted in a counterbore in the wall of the purging chamber in the seal housing member. Thus the seal itself rotates with the seal housing and the transfer member as the assembly comprising the sampling head, dividing means and seal housing member is rotated by the drive shaft to select the appropriate inlet port.

In this arrangement, a leak is most likely to occur between the output member and the sealing means, so that gas may flow between the purging chamber and the sample in the output member, but because the purging chamber is flushed with the purging flow portion from the dividing means, the effect of the leak is minimized.

In a practical arrangement a second rotary sealing means is fitted in the wall of the purging chamber and sealingly engages the output member where it enters the purging chamber, thereby sealing the purging chamber from the surrounding atmosphere. This seal typically comprises a conventional rotary shaft seal.

The bore of the output member and the transfer member connecting it to the dividing means should be as small as possible so that the dead volume of the pipework carrying the sample is kept to a minimum.

Preferably also, a hollow elongated exit member is fitted to the seal housing, through which the purging portion must flow to escape from the purging chamber. The exit member should be sufficiently long to substantially prevent diffusion of gas from the atmosphere surrounding the seal housing into the purging chamber. The exit member may comprise a tube disposed radially on the housing member and opposite the rigid second tube connecting the sampling head with the drive shaft.

In a yet further preferred embodiment the valve is disposed in a substantially enclosed housing which has an exit port for venting the unselected streams of fluid and the purging flow portion after it has passed through the purging chamber. Preferably the housing is bounded on one side by the stationary plate member which comprises the inlet ports. The drive shaft is mounted on bearings in the housing and is sealed by a conventional shaft seal into the housing. An exit port is provided on the housing to allow the unselected gas streams and the purging flow portion of the selected gas stream to escape from the housing. In this way a completely enclosed valve can be provided which can be safely used with poisonous or inflammable fluids.

BRIEF DESCRIPTION OF THE DRAWING

An example of the invention will now be described in greater detail with reference to the figures, in which.

DESCRIPTION OF THE DISCLOSED EMBODIMENT

Figure 1:
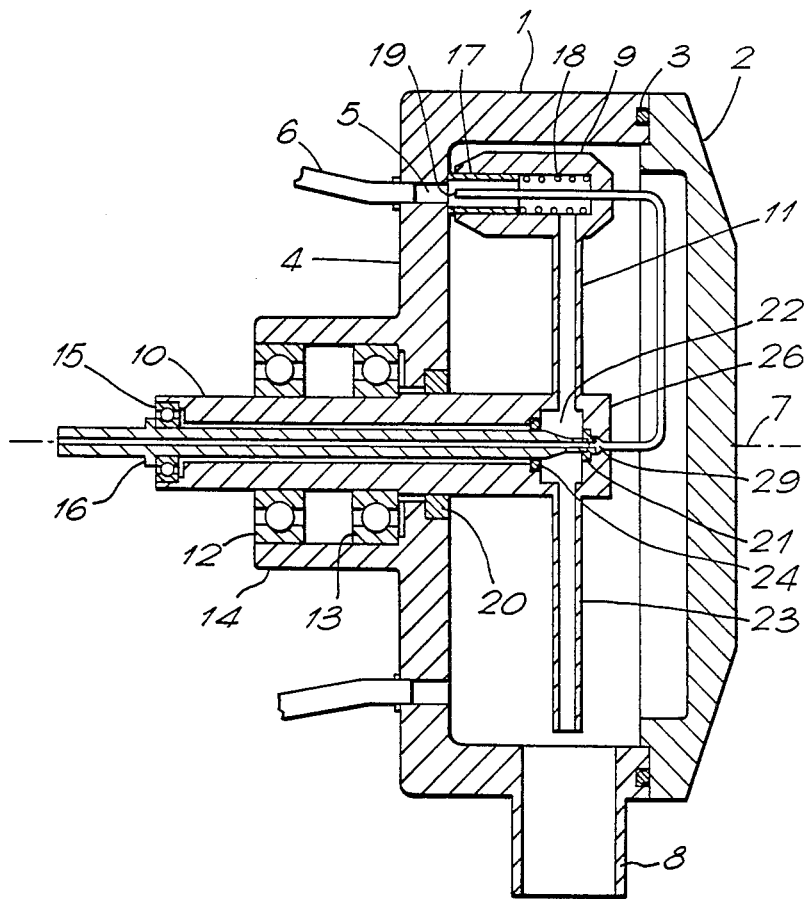
FIG. 1 shows a multi-stream sampling valve constructed according to the invention.

Referring first to FIG. 1, a preferred embodiment of the invention comprises a housing 1 closed by a lid 2 secured to it by several bolts (not shown) and sealed with an '0' ring 3. The rear wall of housing 1 is formed by stationary plate member 4 which contains a plurality of ports 5 located on a circle centered on the valve axis 7. A plurality of stream inlet pipes 6 convey the gas streams to be analyzed into the valve. Pipes 6 may be welded into the back of plate 4 as shown in FIG. 1, or may be attached by unions screwed into plate 4. Typically, at least 20 inlets are provided.

Gas from pipes 6 enters housing 1 through ports 5 and is discharged through an exit port 8 which comprises a large bore pipe.

A movable selecting means comprises a sampling head 9 which is mounted on a drive shaft 10 by means of a rigid tube member 11 extending radially from shaft 10. Shaft 10 is supported by ball-bearing races 12 and 13 which are fixed in a suitable retainer 14 attached to plate member 4, and another ball race 15 which runs on a stationary output member 16.

A rotary shaft seal 20 is provided to ensure that housing 1 is substantially gas tight, and rotary sealing means 24 is provided to prevent purging gas escaping past ball race 15 from the purging chamber 22 (described below).

Drive shaft 10 is rotated by any suitable means in order to position sampling head 9 over any selected one of ports 5 so that the sample flowing in the corresponding inlet pipe 6 is diverted into the sampling head whilst the flows through the remaining ports 5 into housing 1 are unaffected.

Sampling head 9 comprises a sleeve member 17, which is preferably made of a glass filled PTFE or similar material. Sleeve member 17 is a sliding fit inside sampling head 9 and is maintained in sealing contact with plate member 4 by means of spring 18. In order to ensure sealing contact between sleeve member 17 and plate member 4, the surface of plate member 4 is ground flat at least in the region of ports 5. The seal formed between sleeve 17 and plate member 4 need not be of a very high quality, because the pressure differential across it is low, and the flow into head 9 is greatly in excess of that required for the output sample flow.

A sample dividing means is provided, comprising a tube member 19, preferably a narrow-bore tube, which is fitted concentrically within sleeve member 17 and terminates adjacent to plate member 4, as shown in FIG. 1. A sample flow portion comprising a small portion of the gas to be sampled enters the tube 19, whilst the remainder comprises the purging flow portion and leaves the sampling head 9 by tube 11. Tube member 19 is positioned in the centre of sleeve member 17 and samples only the central part of the gas emerging from the selected port 5, thereby minimizing contamination of the sample in tube 19 by small amounts of material which may diffuse into the flow of gas into head 9 through an imperfection in the seal between sleeve 17 and plate member 4.

The other end of sampling tube 19 is connected to a transfer member 29 which passes into a sealing means 21, which is disposed in a seal housing 26 at the end of drive shaft 10. In this way the sample gas passes into stationary output member 16, and is confined to the interior of sealing means 21. A purging chamber 22 is provided inside seal housing 26 adjacent to the exterior of sealing means 21 and is fed with the purging flow portion of excess sample gas from head 9 via tube 11. The purging flow portion escapes from chamber 22 through a hollow elongated exit member 23 into housing 1. Member 23 should be as long as possible to minimize diffusion of gas from housing 1 through member 23, chamber 22 and tube 11, into sampling head 9. In this way the exterior of sealing means 21 is purged by the purging flow portion which has substantially the same composition as the sample flow portion which is flowing through it, so that contamination of the sample through any leak in the sealing means 21 is substantially eliminated.

The bore of output member 16 is preferably equal to that of transfer member 29 in order that the dead volume of the sampling system is kept to a minimum. Thus when sampling head 9 is moved to another of ports 5, the volume of the sample system to be purged with the new selected gas flowing at the low sampling flow rate is limited to the combined volumes of transfer member 29, tube member 19, and output member 16 which can be made very small by the use of, for example, 0.1mm bore tubing.

Figure 2:
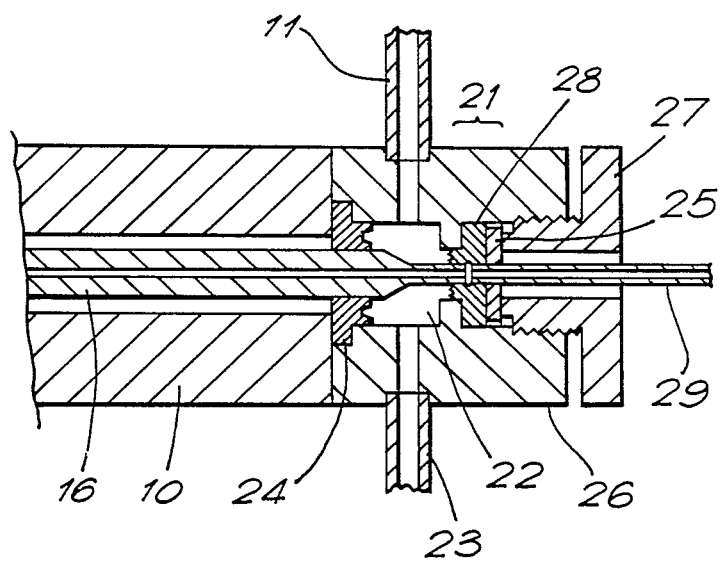
FIG. 2 shows in more detail a rotary shaft seal used in the valve of FIG. 1.

Sealing means 21 is shown in greater detail in FIG. 2. Transfer member 29 is fitted with a flange 25, preferably welded to it. Flange 25 is clamped into a counterbore in seal housing 26 by nut 27 and secures rotary seal 28 in the bottom of the counterbore. Transfer member 29 enters this seal for a short distance. Seal housing 26 is secured to the end of drive shaft 10 by three screws (not shown) and clamps the rotary sealing means 24 in a counterbore opposite that containing seal 28. Tubes 11 and 23 are fitted to seal housing 26 as shown, and purging chamber 22 is formed in housing 26 between them. Output member 16 passes through seal 24 and is then reduced in diameter to exactly the diameter of the portion of transfer member 29 which enters seal 28, and this portion extends into seal 28 almost to the end of transfer member 29. In this way a seal is provided between the rotating transfer member 29 and the stationary output member 16 (seals 24 and 28 of course rotate with shaft 10, housing 26 and transfer member 29).

Seals 28 and 24 should preferably comprise double-lipped rotary shaft seals which are fitted with tensioning springs to hold the seal in good contact with the rotating shaft. Obviously seal 28 must be fitted with the tensioned lips in contact with the output member 16.

Drive shaft 10 is preferably fitted with an indexing mechanism to ensure proper alignment of the sampling head with each of ports 5, and may conveniently be driven by a motor in a conventional way to enable the valve to be automatically operated.

What is claimed is:

1. A valve for providing a sample from any of a plurality of streams of fluid (,) comprising:

a) movable selecting means for selecting one of said plurality of streams while allowing the unselected ones of said streams to discharge;
    b) sample dividing means for dividing the selected one of said streams into a sample flow portion and a purging flow portion;
    c) a stationary output member;
    d) a transfer member movable with said selecting means and adapted to convey said sample flow portion from said selecting means to said stationary output member;
    e) sealing means for connecting said transfer member to said output member and adapted to confine substantially all of said sample flow portion to its interior;
    f) a movable seal housing in which said sealing means is disposed and in which is formed a purging chamber adjacent to at least a part of the exterior of said sealing means, and
    g) means for passing said purging flow portion through said purging chamber.

2. A valve as claimed in claim 1 adapted to provide a sample for analysis by a mass spectrometer from any one of a plurality of streams of gases.

3. A valve as claimed in claim 1 (in which) further comprising a stationary plate member having a plurality of ports to which the streams of fluid to be sampled are connected, and wherein said selecting means comprises a movable sampling head capable of being positioned in alignment with any one of a plurality of said plate member ports, a sleeve member slidable mounted in said sampling head, and means for maintaining said sleeve member in substantially sealing contact with said stationary plate member.

4. A valve according to claim 3 in which said sample dividing means comprises a first tube member disposed inside said sleeve member and terminating adjacent said stationary plate member, said sample flow portion flows through said first tube member and subsequently to said transfer member, and said purging flow portion flows inside said sleeve member and around the exterior of said first tube member.

5. A valve as claimed in claim 1 in which said seal housing is connected to a hollow rotatable drive shaft, at least a part of said output member is disposed within said drive shaft, and said selecting means is connected to said drive shaft by a rigid second tube member which conveys said purging flow portion from said sample dividing means to said purging chamber.

6. A valve as claimed in claim 3 in which said seal housing is connected to a hollow rotatable drive shaft, at least a part of said output member is disposed within said drive shaft, and said sampling head is connected to said drive shaft by a rigid second tube member which conveys said purging flow portion from said sample dividing means to said purging chamber.

7. A valve according to claim 4 in which said seal housing is connected to a hollow rotatable drive shaft, at least a part of said output member is disposed within said drive shaft, and said sampling head is connected to said drive shaft by a rigid second tube member which conveys said purging flow portion from inside said sleeve member to said purging chamber.

8. A valve according to claim 1 in which said output member extends into said purging chamber and in which there is provided a sealing means in a wall of said purging chamber which sealingly engages the exterior of said output member.

9. A valve according to claim 5 in which said output member extends into said purging chamber and in which there is provided a rotary sealing means in a wall of said purging chamber which sealingly engages the exterior of said output member.

10. A valve according to claim 6 in which said output member extends into said purging chamber and in which there is provided a rotary sealing means in a wall of said purging chamber which sealingly engages the exterior of said output member.

11. A valve according to claim 7 in which said output member extends into said purging chamber and in which there is provided a rotary sealing means in a wall of said purging chamber which sealingly engages the exterior of said output member.

12. A valve according to claim 1 in which a hollow elongated exit member is provided on said seal housing, through which exit member said purging flow passes on leaving said purging chamber.

13. A valve according to claim 1 which is disposed in a substantially enclosed housing having an exit port for venting the unselected ones of said plurality of streams of fluid and said purging flow portion after it has passed through said purging chamber.

14. A valve according to claim 12 which is disposed in a substantially enclosed housing having an exit port for venting the unselected ones of said plurality of streams of fluid and said purging flow portion after it has passed through said purging chamber.

15. A valve according to claim 3 which is disposed in a substantially enclosed housing having an exit port for venting the unselected ones of said plurality of streams of fluid and said purging flow portion after it has passed through said purging chamber, and in which said housing comprises at least a part of said stationary plate member.

16. A valve according to claim 4 which is disposed in a substantially enclosed housing having an exit port for venting the unselected ones of said plurality of streams of fluid and said purging flow portion after it has passed through said purging chamber, and in which said housing comprises at least a part of said stationary plate member.

17. A valve according to claim 6 which is disposed in a substantially enclosed housing having an exit port for venting the unselected ones of said plurality of streams of fluid and said purging flow portion after it has passed through said purging chamber, and in which said housing comprises at least a part of said stationary plate member.

18. A valve according to claim 7 which is disposed in a substantially enclosed housing having an exit port for venting the unselected ones of said plurality of streams of fluid and said purging flow portion after it has passed through said purging chamber, and in which said housing comprises at least a part of said stationary plate member.

19. A valve according to claim 10 which is disposed in a substantially enclosed housing having an exit port for venting the unselected ones of said plurality of streams of fluid and said purging flow portion after it has passed through said purging chamber, and in which said housing comprises at least a part of said stationary plate member.

20. A valve according to claim 11 which is disposed in a substantially enclosed housing having an exit port for venting the unselected ones of said plurality of streams of fluid and said purging flow portion after it has passed through said purging chamber, and in which said housing comprises at least a part of said stationary plate member.

* * * * *